US012572507B2

(12) United States Patent
Sawada et al.

(10) Patent No.: US 12,572,507 B2
(45) Date of Patent: Mar. 10, 2026

(54) DATA PROCESSING SYSTEM, DATA PROCESSING METHOD, AND COMPUTER PROGRAM FOR EXECUTING DATA PROCESSING METHOD USING INFORMATION PROCESSING DEVICE

(71) Applicant: SHIMADZU CORPORATION, Kyoto (JP)

(72) Inventors: Ryuji Sawada, Kyoto (JP); Shuhei Yamamoto, Kyoto (JP); Takeshi Ono, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 18/028,629

(22) PCT Filed: Apr. 27, 2021

(86) PCT No.: PCT/JP2021/016767
§ 371 (c)(1),
(2) Date: Mar. 27, 2023

(87) PCT Pub. No.: WO2022/070494
PCT Pub. Date: Apr. 7, 2022

(65) Prior Publication Data
US 2023/0334019 A1 Oct. 19, 2023

(30) Foreign Application Priority Data
Sep. 30, 2020 (JP) ................................. 2020-164499

(51) Int. Cl.
G06F 16/583 (2019.01)
G06F 16/16 (2019.01)
G06F 16/185 (2019.01)
C12M 1/00 (2006.01)

(52) U.S. Cl.
CPC .......... *G06F 16/168* (2019.01); *G06F 16/164* (2019.01); *G06F 16/185* (2019.01); *G06F 16/5862* (2019.01); *C12M 1/00* (2013.01)

(58) Field of Classification Search
CPC ............................................ G06F 16/50–5862
See application file for complete search history.

(56) References Cited

U.S. PATENT DOCUMENTS

2006/0104520 A1* 5/2006 Kraus ..................... G06F 16/55
707/E17.026
2009/0177988 A1* 7/2009 Martins ................. G06F 16/283
707/999.005

(Continued)

FOREIGN PATENT DOCUMENTS

CN 102081497 A 6/2011
JP 2006-031593 A 2/2006

OTHER PUBLICATIONS

Written Opinion for PCT/JP2021/016767 dated Jul. 20, 2021.

(Continued)

*Primary Examiner* — Robert W Beausoliel, Jr.
*Assistant Examiner* — Nirav K Khakhar
(74) *Attorney, Agent, or Firm* — Sughrue Mion, PLLC

(57) ABSTRACT

A data processing system (1) including an information processing device (2) and an information display device (4), in which the information processing device (2) includes a data registration part (8) configured to register a plurality of pieces of data acquired by a predetermined data acquisition device (6) as data handled by the data processing system (1) in a state where each piece of the data and at least one type of accompanying information of each piece of the data are associated with each other, a registration data holder (10) that holds data registered by the data registration part (8), a data tree creator (12) configured to group the plurality of pieces of data held in the registration data holder (10) by (Continued)

using the accompanying information of an optionally selected type so that pieces of the data having a common piece of the accompanying information belong to a same group, and to create a data tree virtually indicating a state in which a plurality of pieces of the data are distributed into groups, and an information display part (14) configured to display a data tree created by the data tree creator (12) on the information display device (4).

2 Claims, 10 Drawing Sheets

(56) References Cited

U.S. PATENT DOCUMENTS

| | | | |
|---|---|---|---|
| 2011/0122153 A1* | 5/2011 | Okamura | G09B 29/106 |
| | | | 345/629 |
| 2021/0075754 A1* | 3/2021 | Spiry | G06F 18/23 |

OTHER PUBLICATIONS

International Search Report for PCT/JP2021/016767 dated Jul. 20, 2021.
Japanese Office Action dated Jan. 16, 2024 in Application No. 2022-553454.
Chinese Office Action issued Apr. 17, 2024 in Application No. 202180061854.9.
Communication dated Aug. 27, 2024, issued in Chinese Application No. 202180061854.9.
Communication issued Jan. 16, 2025 in Chinese Application No. 202180061854.9.

\* cited by examiner

Start

101 Select data to be registered and input accompanying information

102 Associate data and accompanying information

103 Register data

104 Store registered data

End

FIG. 3

Registration of data

Passage number :   0

Number of culture days :   0

Registration data :

Cancel     Register

DATA PROCESSING SYSTEM, DATA PROCESSING METHOD, AND COMPUTER PROGRAM FOR EXECUTING DATA PROCESSING METHOD USING INFORMATION PROCESSING DEVICE

This Application is a National Stage of International Application No. PCT/JP2021/016767 filed Apr. 27, 2021, claiming priority to Japanese Patent Application No. 2020-164499 filed Sep. 30, 2020.

TECHNICAL FIELD

The present invention relates to a data processing system, a data processing method, and a computer program for executing a data processing method using an information processing device.

BACKGROUND ART

In cell culture, it is common to image the inside of each well using a microscope in order to observe a state in each well of a culture plate. A captured image in each well needs to be managed in association with accompanying information such as a passage number of a cell, the number of culture days, a position of each well in a culture plate, and a type of microscope used for imaging. For this reason, when each piece of image data is stored in a personal computer (PC), a method in which accompanying information of data is added to a file name of each piece of image data, a folder configuration of a hierarchical structure formed by a plurality of folder groups to which accompanying information of an image is added is created, and each piece of image data is distributed and stored in a folder that matches accompanying information is often employed.

SUMMARY OF THE INVENTION

Problems to be Solved by the Invention

In the method of managing a large number of pieces of image data by a folder configuration of a hierarchical structure as described above, rules regarding sorting into a folder, naming of a file name, and the like may vary depending on an operator. For this reason, there has been a problem that it is difficult for a person other than an operator who has first organized data to grasp what data is stored in which folder.

Further, when a folder configuration has a hierarchical structure, work of simultaneously checking and comparing a plurality of pieces of data stored in different folders becomes complicated, which may cause a work error. In a folder configuration having a hierarchical structure, a child folder or a data file is associated with a lower layer of a parent folder. Therefore, it is not easy to reconstruct another data configuration by changing the structure of the folder configuration once constructed.

The present invention has been made in view of the above problem, and an object of the present invention is to facilitate management of a large number of pieces of data having different accompanying information.

Solutions to the Problems

A data processing system according to the present invention is a data processing system including an information processing device and an information display device. The information processing device includes a data registration part configured to register a plurality of pieces of data acquired by a predetermined data acquisition device as data handled by the data processing system in a state where each piece of the data and at least one type of accompanying information of each piece of the data are associated with each other, a registration data holder that holds data registered by the data registration part, a data tree creator configured to group the plurality of pieces of data held in the registration data holder by using the accompanying information of an optionally selected type so that pieces of the data having a common piece of the accompanying information belong to a same group, and to create a data tree virtually indicating a state in which a plurality of pieces of the data are distributed into groups, and an information display part configured to display a data tree created by the data tree creator on the information display device.

A data processing method according to the present invention includes a registration step of registering a plurality of pieces of data acquired by a predetermined data acquisition device in a state where the data and at least one type of accompanying information of each piece of the data are associated with each other, a tree creation step of grouping a plurality of pieces of the data registered in the registration step by using the accompanying information of an optionally selected type so that pieces of the data having a common piece of the accompanying information belong to the same group, and creating a data tree virtually indicating a state in which the plurality of pieces of data are distributed into groups, and a display step of displaying a data tree created in the tree creation step on a predetermined information display device.

Here, the "predetermined data acquisition device" includes a microscope for imaging the inside of a cell culture well, an analysis device for analyzing an image acquired by such a microscope, and the like. In a case where the data acquisition device is a microscope that images the inside of a cell culture well, acquired data is data of an image. Further, in a case where the data acquisition device is an analysis device that analyzes such an image, acquired data is data of a numerical value such as the number of cells in the image and a ratio of an area occupied by a cell region in the image. The "accompanying information" of these pieces of data can include information on an imaged well (such as the position of a well in a culture plate), and types of information such as a type of microscope used for imaging, the number of culture days of a cell, and a passage number of a cell.

In the present invention, instead of distributing a plurality of pieces of data acquired by a predetermined data acquisition device into a plurality of folders forming a specific hierarchical structure for management, accompanying information is associated with each of a plurality of pieces of data for management. The accompanying information associated with each piece of data plays a role as a label indicating an attribute of each piece of data, and when the user selects a type of accompanying information that the user desires to effectively function as a label, each piece of data is grouped such that data having common accompanying information of the selected type (that is, information such as a numerical value input as accompanying information of the type is the same) belongs to the same group, and a virtual data tree is created and displayed as if a folder configuration having a hierarchical structure is constructed.

Effects of the Invention

In the data processing system and the data processing method according to the present invention, when the user selects a type of accompanying information that the user desires to effectively function as a label, each piece of data is grouped such that data having common accompanying information of the selected type belongs to the same group, and a virtual data tree is automatically created and displayed as if a folder configuration having a hierarchical structure is constructed. Therefore, even if the user does not actually construct a folder configuration having a hierarchical structure, it is possible to easily manage a large number of pieces of data having different pieces of accompanying information.

BRIEF DESCRIPTION OF THE DRAWINGS

FIG. 3 is an example of a screen displayed at the time of data registration.

EMBODIMENT OF THE INVENTION

Hereinafter, an embodiment of a data processing system, a data processing method, and a computer program according to the present invention will be described with reference to the drawings.

Figure 1:
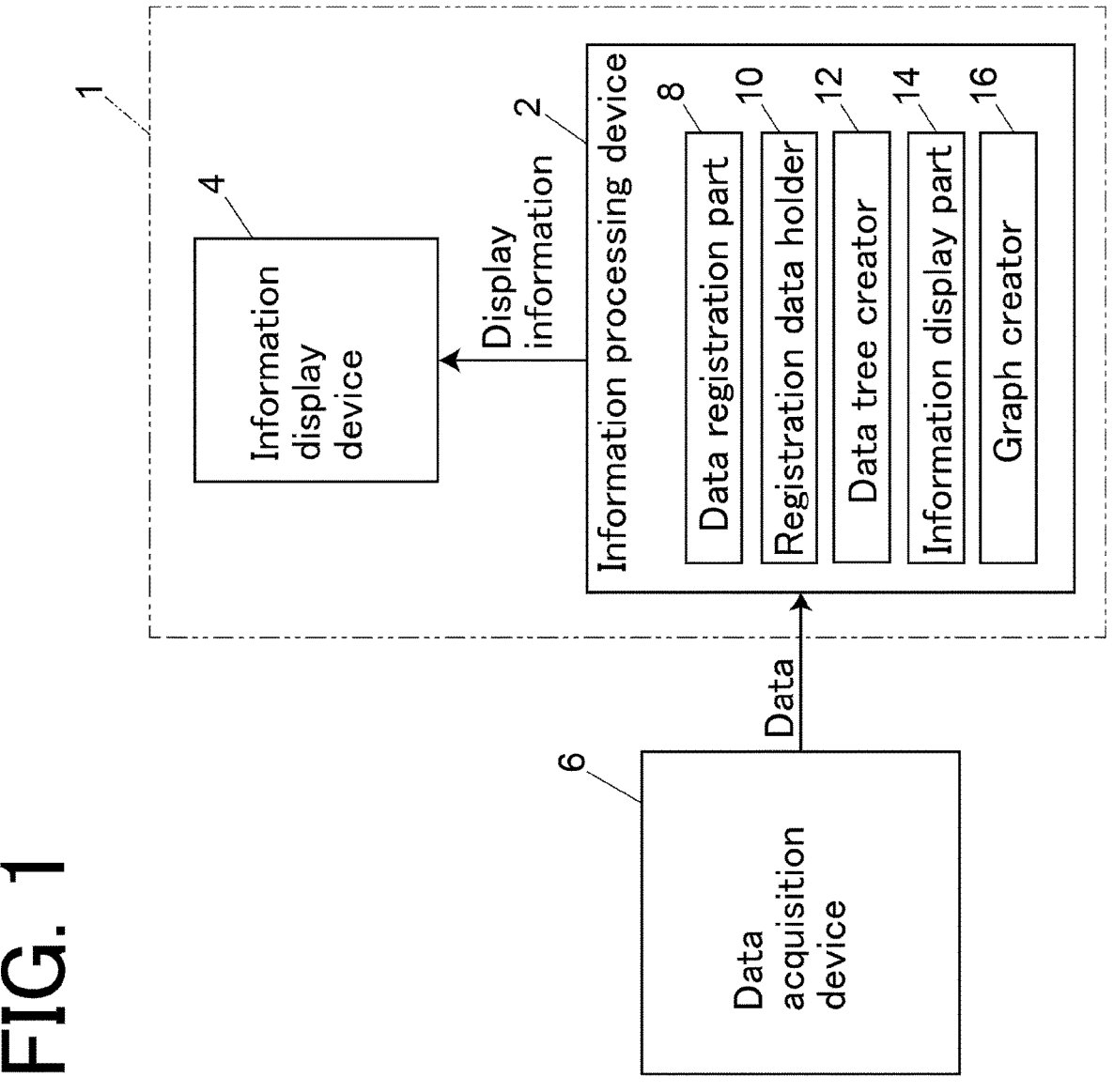
FIG. 1 is a block diagram illustrating an example of a data processing system.

FIG. 1 illustrates a schematic configuration of the data processing system.

A data processing system 1 includes an information processing device 2 and an information display device 4. The information processing device 2 has a function of fetching a plurality of pieces of data acquired by a data acquisition device 6 and performing predetermined processing. The information processing device 2 is a computer device (for example, a personal computer) including an information storage medium such as a hard disk drive and an electronic circuit including a central processing unit (CPU), in which a computer program for realizing each function to be described later is introduced. The information display device 4 is a display (for example, a liquid crystal display) communicably connected to the information processing device 2. Examples of the data acquisition device 6 include a microscope for imaging the inside of each well of a cell culture plate, an analysis device for analyzing an image acquired by such a microscope, and the like. Note that, although not illustrated in the present example, in a case where the information processing device 2 has a function of analyzing image data captured from a microscope, the information processing device 2 also functions as the data acquisition device 6 for acquiring analysis data.

The information processing device 2 includes a data registration part 8, a registration data holder 10, a data tree creator 12, an information display part 14, and a graph creator 16. The data registration part 8, the data tree creator 12, the information display part 14, and the graph creator 16 are functions realized by a CPU executing a predetermined computer program installed in the information processing device 2. The registration data holder 10 is a function realized by a partial storage area of an information storage medium in the information processing device 2.

The data registration part 8 is configured to register data acquired by the data acquisition device 6 as data handled by the data processing system 1 in association with accompanying information of the data. The registration data holder 10 is configured to hold data registered by the data registration part 8.

Figure 2:
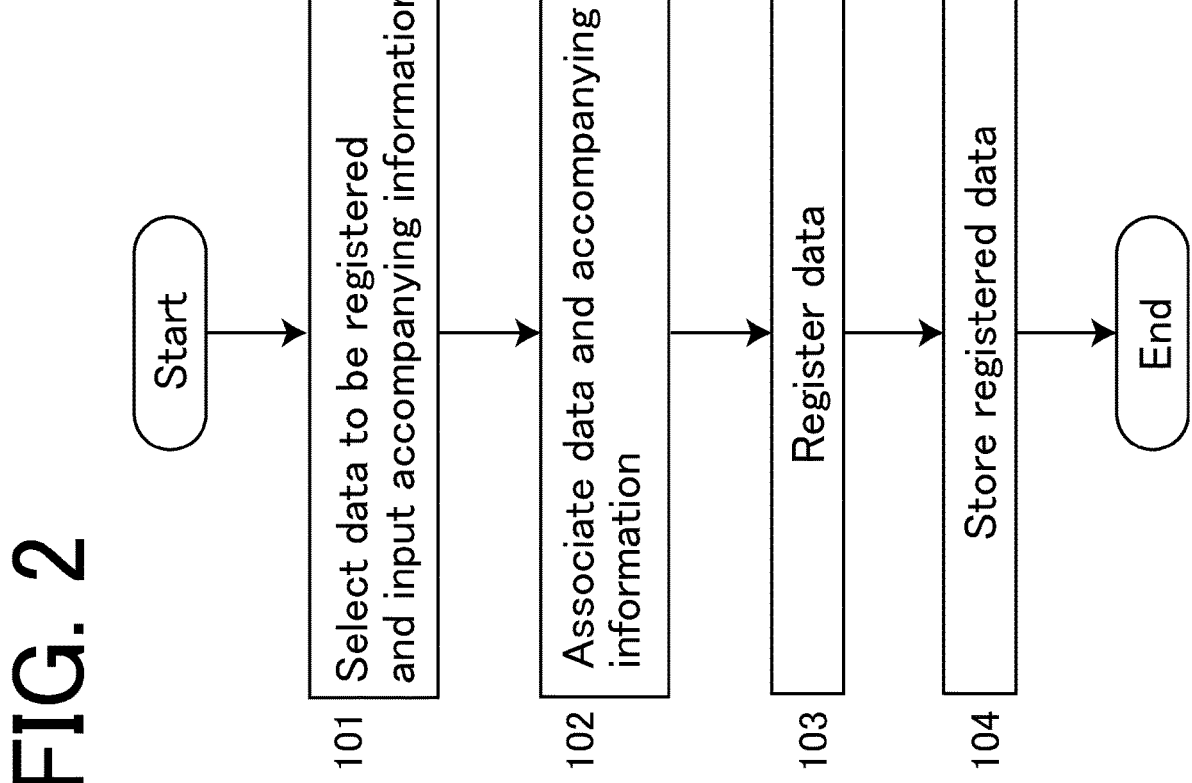
FIG. 2 is a flowchart illustrating an example of a series of operations related to data registration in the example.

A series of operations related to data registration will be described with reference to FIGS. 2 and 3.

Figure 3:
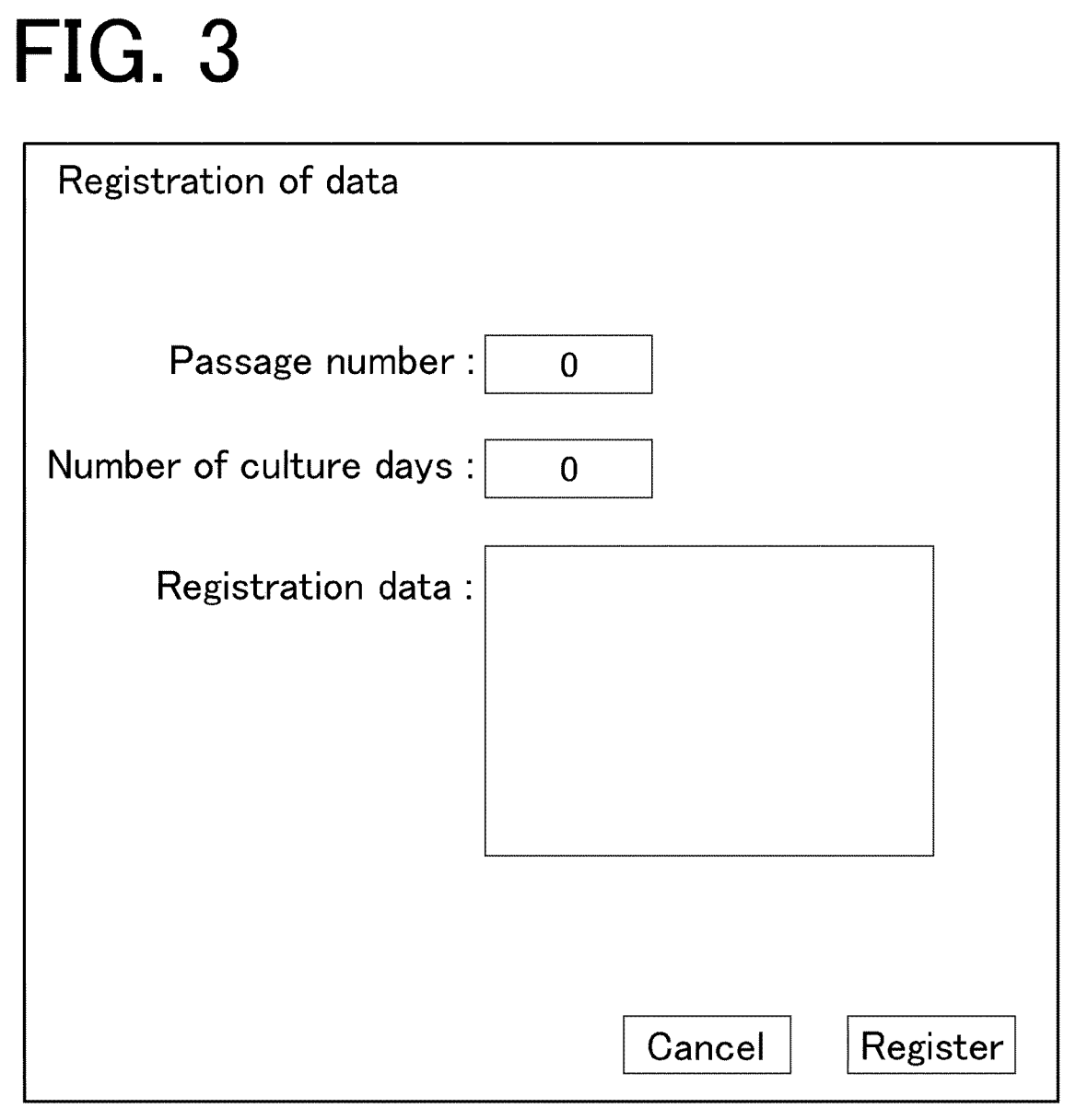

When the user inputs an instruction to register data to the information processing device 2, the data registration part 8 displays a data registration screen as illustrated in FIG. 3 on the information display device 4. On the displayed data registration screen, the user selects data to be registered with reference to data that is fetched or can be fetched by the information processing device 2, and inputs accompanying information of the data (Step 101).

FIG. 3 is an example of a registration screen of image data of a cell culture well imaged by a microscope, and a passage number of a cell and the number of culture days are input as accompanying information of data. When the user selects data to be registered, inputs accompanying information of the data, and determines the content (presses a registration button in FIG. 3), the data registration part 8 associates the selected data with the input accompanying information (Step 102), and registers the data as data to be handled by the data processing system 1 (Step 103). The data registered by the data registration part 8 is stored in the registration data holder 10 in a state of being associated with the accompanying information (Step 104).

Figure 4:
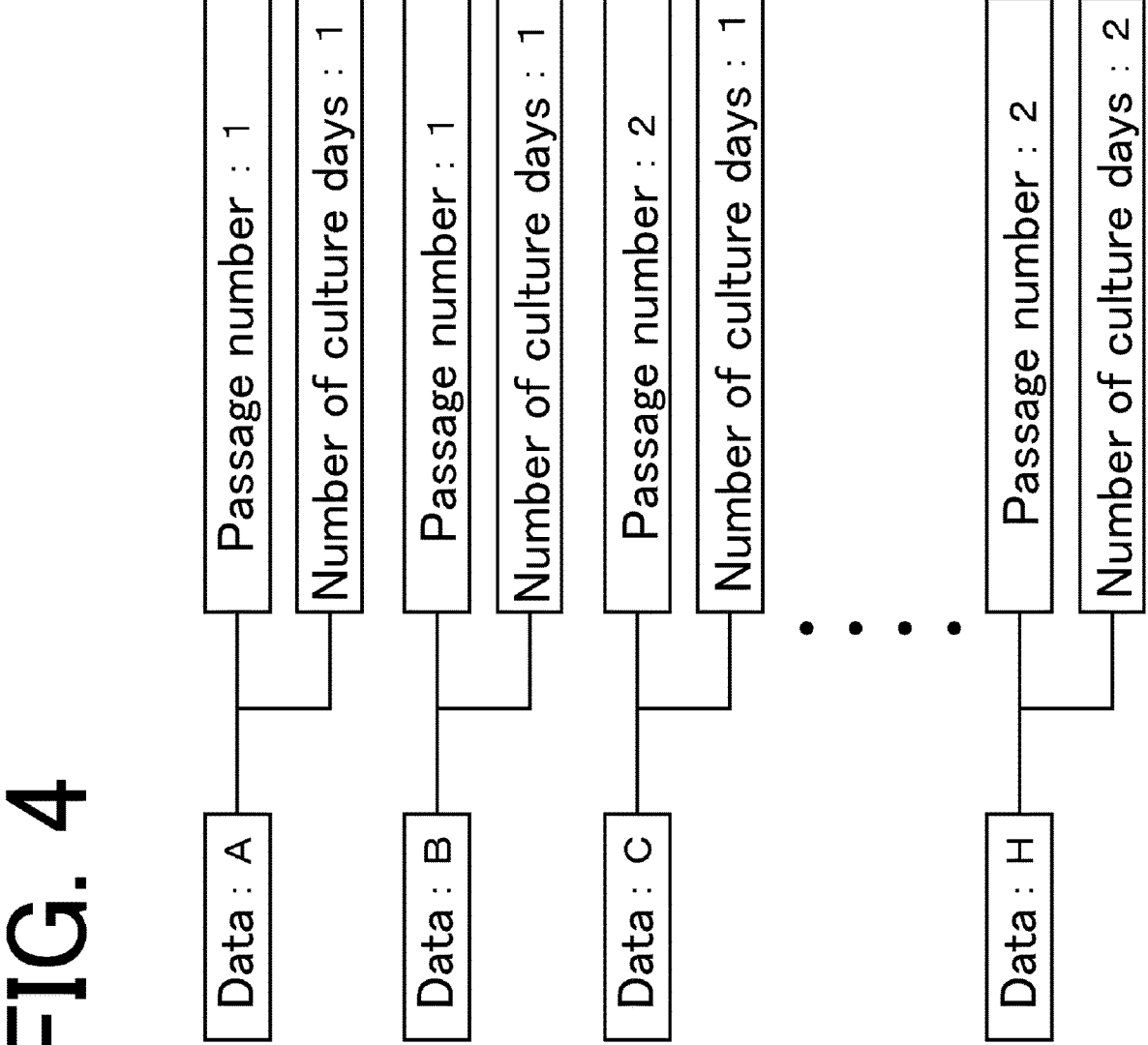
FIG. 4 is a conceptual diagram of a data configuration after a plurality of pieces of data are registered.

The above series of operations are executed for all data to be handled by the data processing system 1. As a result, as illustrated in FIG. 4, a plurality of pieces of data exist in the registration data holder 10 in a state of being associated with accompanying information of a common type.

The description will be continued with reference to FIG. 1 again. The data tree creator 12 of the information processing device 2 is configured to group a plurality of pieces of data held in the registration data holder 10 according to accompanying information associated with each piece of data, and create a virtual data tree having a hierarchical structure. The data tree is a format indicating a list of states in which each piece of data is distributed to a plurality of folders having titles corresponding to accompanying information of each piece of data. The creation of a data tree by the data tree creator 12 is executed, for example, when a plurality of pieces of data held in the registration data holder 10 are presented to the user. The information display part 14 is configured to display a virtual data tree created by the data tree creator 12 on the information display device 4.

Figure 5:
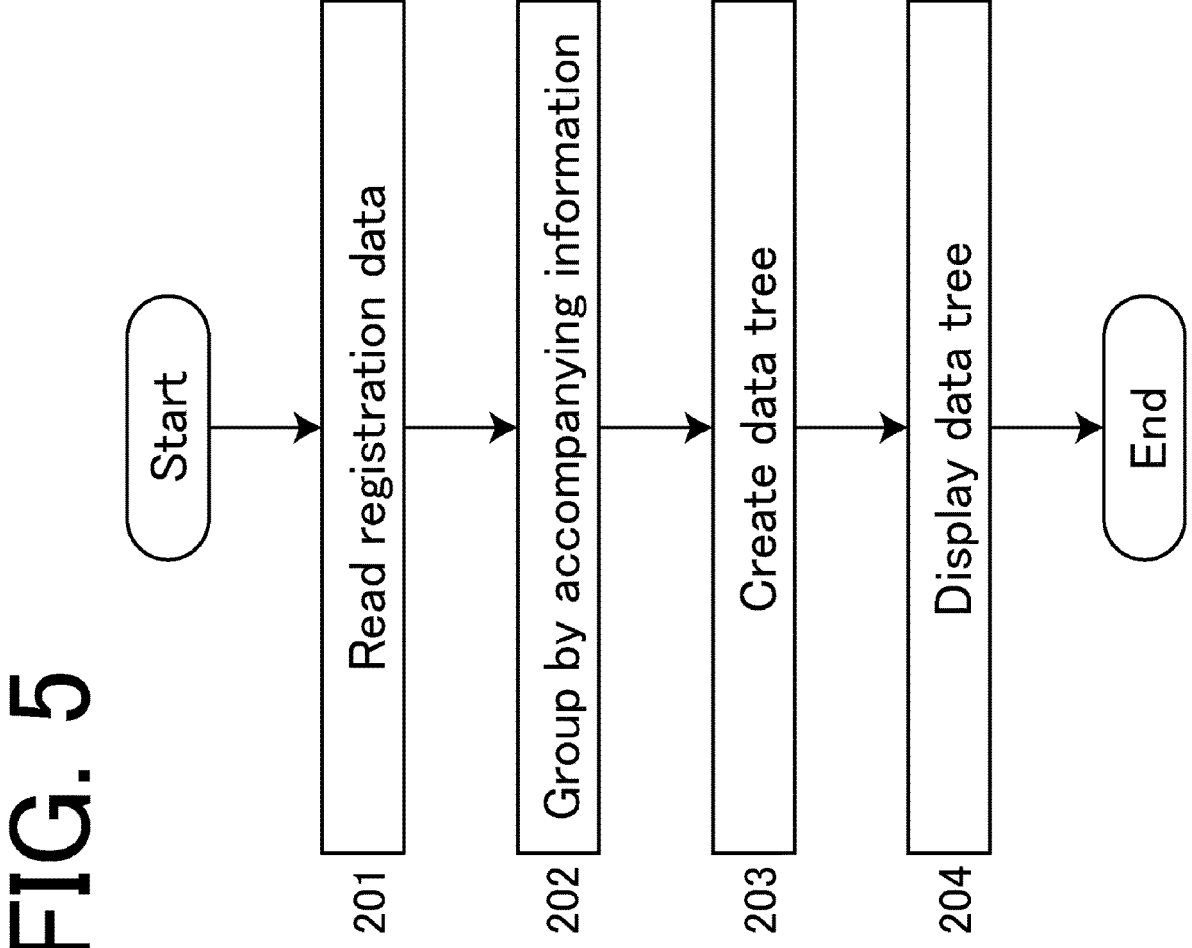
FIG. 5 is a flowchart illustrating operation for displaying a virtual data tree in the example.

A series of operations related to creation of a data tree will be described with reference to FIG. 5.

For example, when the user intends to refer to data registered in the data processing system 1, the data tree creator 12 reads target registration data from the registration data holder 10 (Step 201), groups the read registration data using accompanying information associated with the registration data (Step 202), and creates a data tree having a hierarchical structure based on the grouping (Step 203). The information display part 14 displays the virtual data tree created by the data tree creator 12 on the information display device 4 (Step 204).

Here, in the accompanying information associated with the registration data, whether or not to use the accompanying information for grouping and priority order used for grouping are set in advance. These settings can be optionally changed by the user. For example, in default setting, all pieces of accompanying information are used for grouping, and default priority order is set for the accompanying information. When the user attempts to refer to data, the data tree creator 12 creates a data tree based on default priority order, and the created data tree is displayed on the information display device 4 together with accompanying information used for grouping and a grouping condition indicating a priority relationship between the accompanying information. The user can switch whether each piece of accompanying information is used for grouping (valid) or not used for grouping (invalid) and change a priority relationship of each piece of accompanying information, and can optionally change a grouping condition. Such operation of changing a grouping condition can be performed by dragging with a mouse, key input, or the like. When a grouping condition is changed by the user, a data tree based on a changed grouping condition is immediately created by the data tree creator 12 and displayed on the information display device 4. By the above, a data tree based on a grouping condition desired by the user is displayed in real time.

Figure 6:
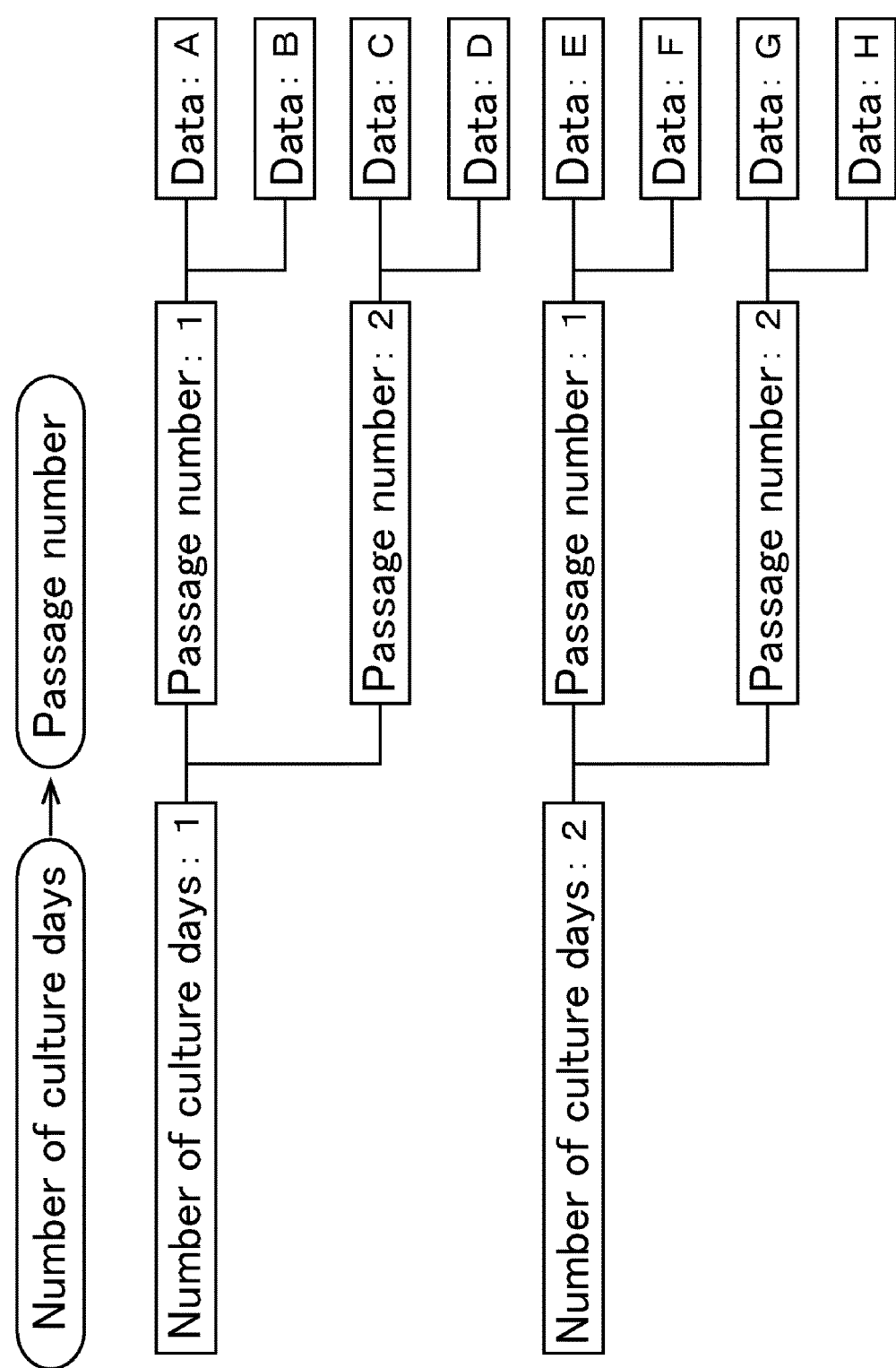
FIG. 6 is an example of a virtual data tree.

FIG. 6 is an example of a virtual data tree created by the data tree creator 12. Each piece of registered data A to H is associated with accompanying information of types "number of culture days" and "passage number", and all types of accompanying information are set to be used for grouping. At a top portion, types of accompanying information to be used for grouping and a grouping condition indicating a priority relationship between them are displayed, and in this example, "number of culture days" is set to be higher in priority order than "passage number". In this setting, first, data is grouped into a group of "Number of culture days: 1" (Data A to D) and a group of "Number of culture days: 2" (Data E to F) in a manner that data having a common number of culture days belongs to the same group, and, in each of the groups, data is grouped into a group of "Passage number: 1" and a group of "Passage number: 2". As a result, a data tree having a hierarchical structure as illustrated in the diagram is created.

Figure 7:
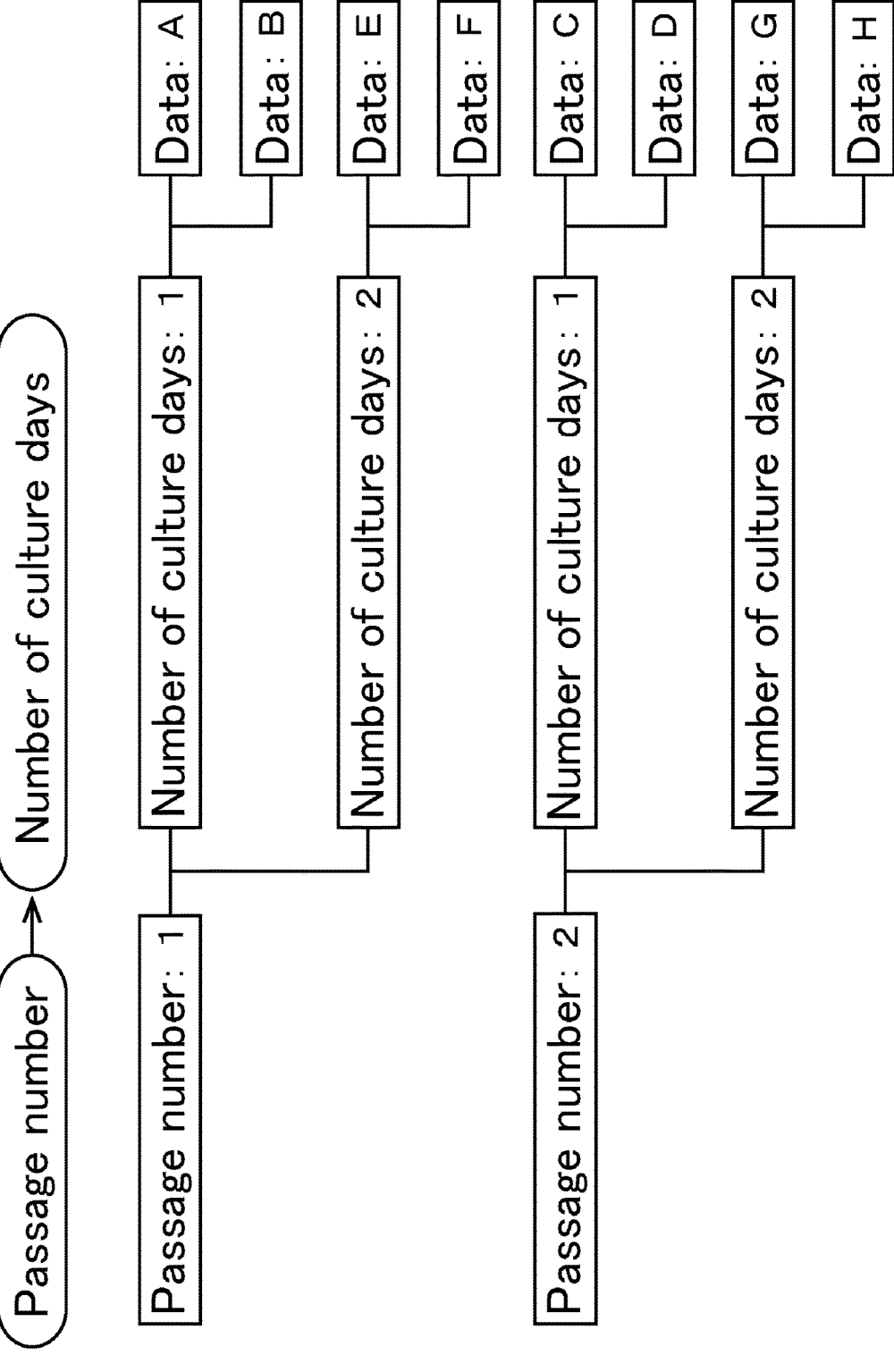
FIG. 7 is an example of a data tree created when priority order of accompanying information used for grouping is changed from the data tree of FIG. 6.

FIG. 7 is an example of a data tree created when a priority relationship of accompanying information is changed from the data tree of FIG. 6. When the user sets a passage number to be higher in priority order than the number of culture days, data is first grouped into a group of "Passage number: 1" and a group of "Passage number: 2" in a manner that data having the same passage number belongs to the same group, and, in each of the groups, data is grouped into a group of "Number of culture days: 1" and a group of "Number of culture days: 2". As a result, a data tree having a hierarchical structure as illustrated in the diagram is created.

Figure 8:
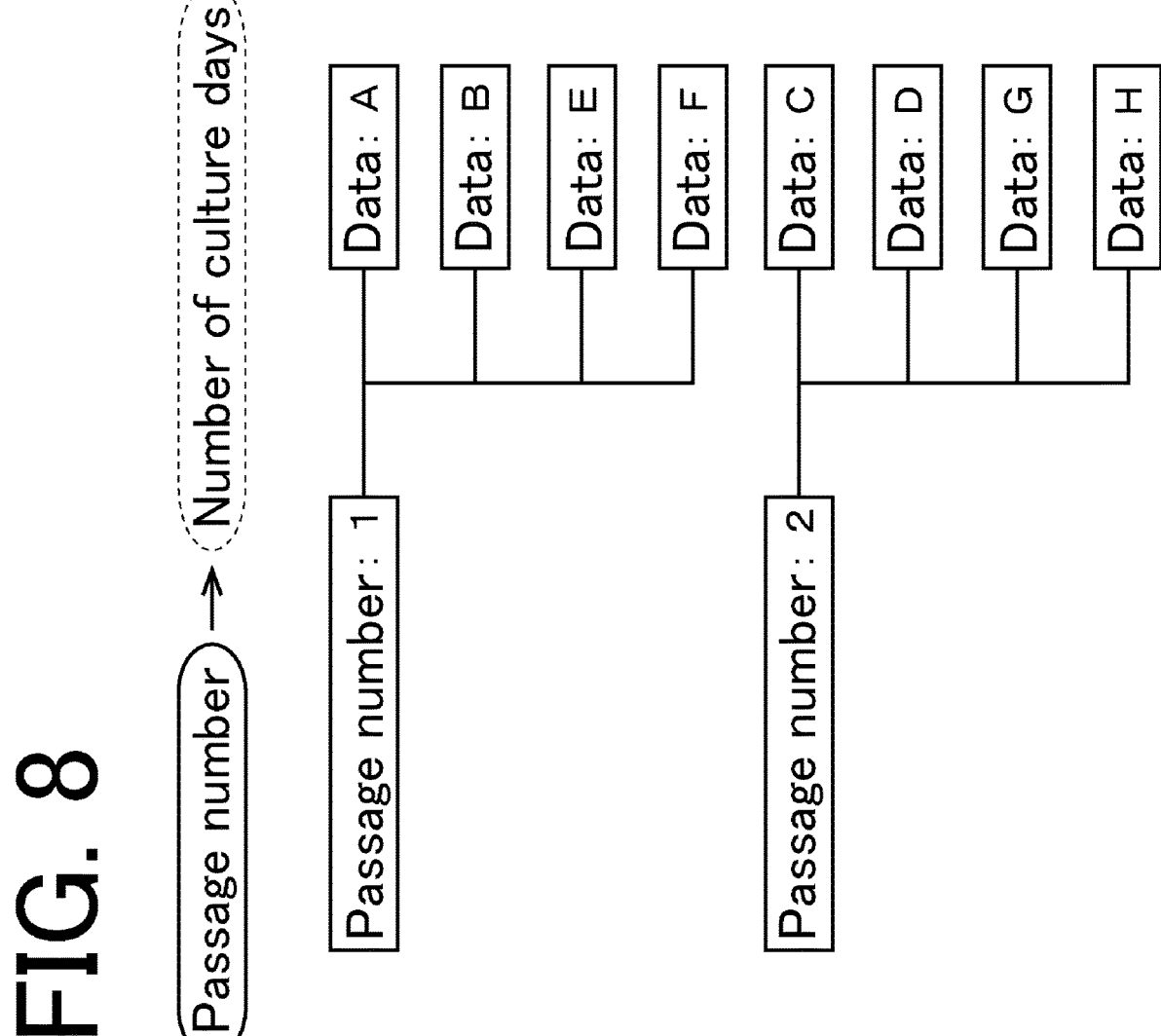
FIG. 8 is an example of a data tree created when one piece of accompanying information used for grouping is invalidated.

FIG. 8 is an example of a data tree created when the accompanying information "Number of culture days" used for grouping in the example of FIG. 7 is set to invalid (not used for grouping). In this example, since the accompanying information "number of culture days" is invalidated, pieces of Data A to H are grouped only by the accompanying information "passage number", and a data tree including a group of "Passage number: 1" and a group of "Passage number: 2" is created.

As described above, in the data processing system 1 according to the present example, when the user attempts to refer to a plurality of pieces of registered data, optional accompanying information can be grouped using an optional priority relationship and data can be displayed as a data tree.

Note that "data" handled by the data processing system 1 is image data in a case where the data acquisition device 6 is a microscope that captures an image of a cell culture well. However, in a case where the information processing device 2 has a function of performing analysis processing of the image, numerical data such as "number of cells" and "area ratio of a cell region" obtained by analysis processing of image data performed by the information processing device 2 itself may also be included in the "data". In this case, the data registration part 8 can be configured to register numerical data obtained by analysis processing performed on image data in association with accompanying information such as "number of culture days" and "passage number" associated with the original image data, and cause the registration data holder 10 to hold the numerical data.

Returning to FIG. 1, in a case where registration data is numerical data, the graph creator 16 of the information processing device 2 is configured to create a graph based on a data tree created by the data tree creator 12, using a numerical value of each piece of registration data and accompanying information associated with each piece of registration data. An example of a relationship between a data tree created by the data tree creator 12 and a graph created by the graph creator 16 will be described below with reference to FIGS. 9 and 10.

Figure 9:
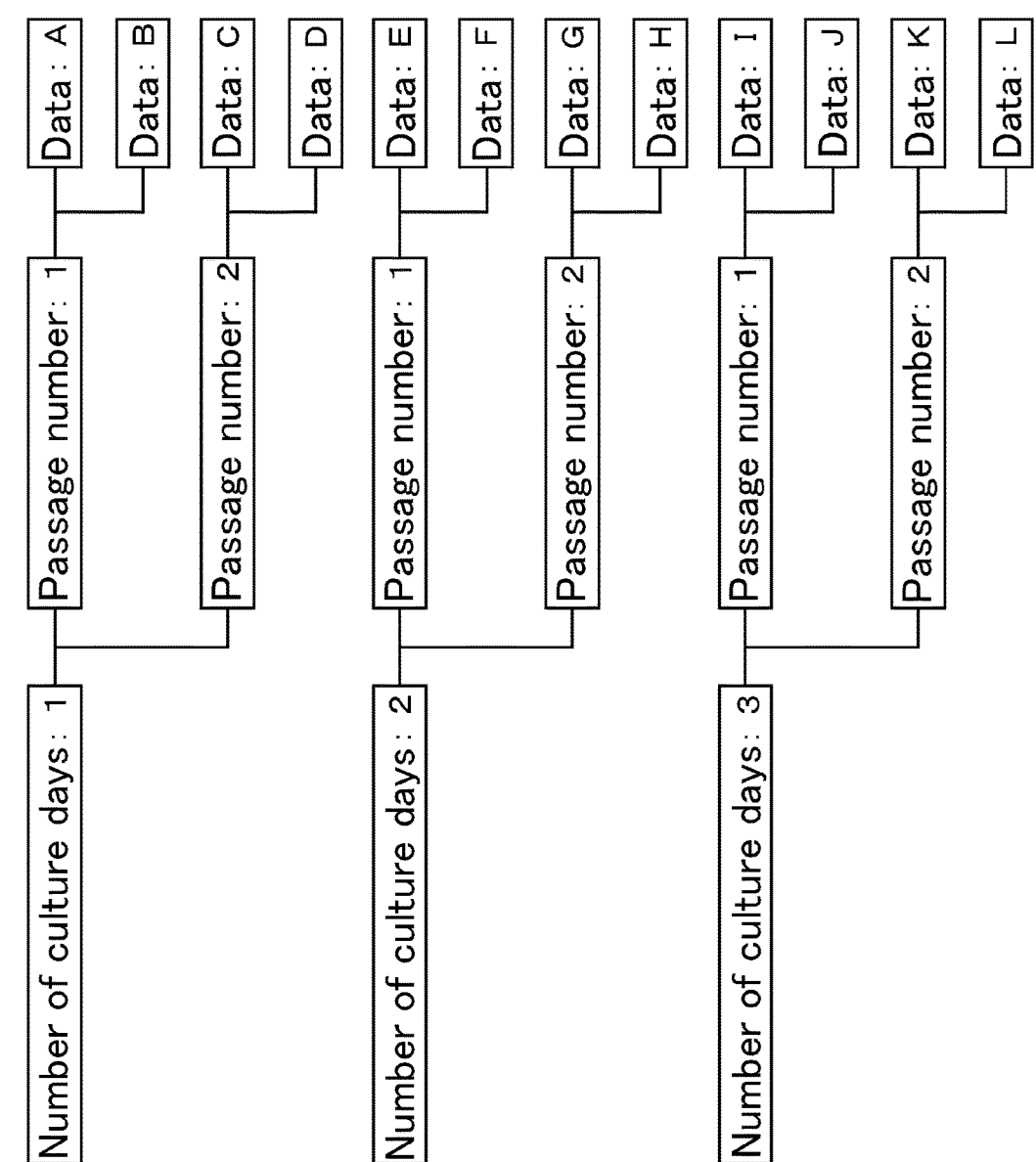
FIG. 9 is an example of a data tree on which a graph is created.
Figure 10:
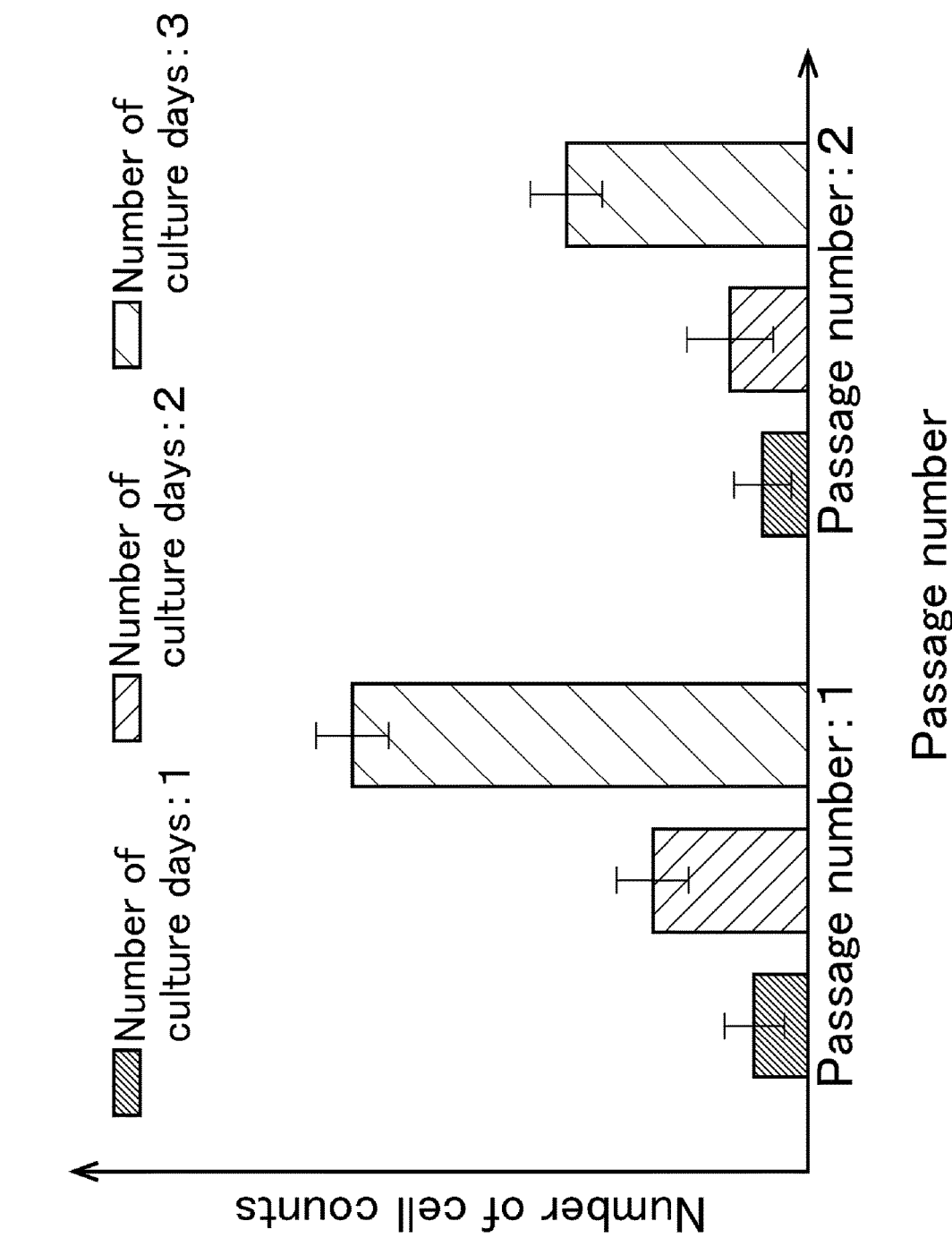
FIG. 10 is an example of a graph created based on the data tree of FIG. 9.

FIG. 9 is a data tree illustrating a state in which pieces of registered numerical data A to L are grouped by accompanying information "number of culture days" and "passage number". When such a data tree is created, for example, when the user gives an instruction to analyze data, as illustrated in FIG. 10, the graph creator 16 creates a graph in which "passage number" which is accompanying information at the lowermost layer (lowest in priority order) is taken on the horizontal axis, a numerical value (the number of cell counts here) representing a numerical value of each piece of data is taken on the vertical axis, and "number of culture days" which is accompanying information second from the lowermost layer is taken as a legend. In this example, since there are two pieces of numerical data (for example, pieces of numerical data of Number of culture days: 1 and Passage number: 1 are Data A and Data B) for each number of culture days, an average value of them is displayed on the graph.

A graph created by the graph creator 16 is not limited to a bar graph as illustrated in FIG. 10, and may be various graphs such as a line graph and a pie chart.

Note that the example described above is merely an example of an embodiment of the present invention. The embodiment of the present invention is as described below.

An embodiment of the data processing system according to the present invention is a data processing system including an information processing device and an information display device. The information processing device includes a data registration part configured to register a plurality of pieces of data acquired by a predetermined data acquisition device as data handled by the data processing system in a state where each piece of the data and at least one type of accompanying information of each piece of the data are associated with each other, a registration data holder that holds data registered by the data registration part, a data tree creator configured to group the plurality of pieces of data held in the registration data holder by using the accompanying information of an optionally selected type so that pieces of the data having a common piece of the accompanying information belong to a same group, and to create a data tree virtually indicating a state in which a plurality of pieces of the data are distributed into groups, and an information display part configured to display a data tree created by the data tree creator on the information display device.

In a first aspect of the embodiment of the data processing system, the data registration part is configured to perform registration of the plurality of pieces of data in a state where a plurality of types of the accompanying information are associated with each of a plurality of pieces of the data, and the data tree creator is configured, in a case where a plurality of types of the accompanying information are set to be used for the grouping, to create the data tree having a hierarchical structure in which the accompanying information of a type that is higher in priority order set in advance for each type of the accompanying information is located on a higher layer.

In the first aspect, the information processing device is configured so that the priority order is optionally changeable. In this manner, the user can optionally change a hierarchical structure of a data tree, and data management is facilitated.

In a second aspect of the embodiment of the data processing system, the data is an image of cell culture or a numerical value acquired by analysis of the image. In that case, at least one of a passage number and the number of culture days can be included as the accompanying information. This second aspect can be combined with the first aspect.

In a third aspect of the embodiment of the data processing system, the data is a numerical value obtained by analysis. In this case, the information processing device may further include a graph creator that creates a graph having a first axis and a second axis based on a structure of the data tree created by the data tree creator, wherein the first axis indicates each numerical value of a plurality of pieces of the data, and the second axis indicates at least one piece of the accompanying information used for the grouping. This third aspect can be combined with the first aspect and/or the second aspect described above.

An embodiment of the data processing method according to the present invention includes a registration step of registering a plurality of pieces of data acquired by a predetermined data acquisition device in a state where the data and at least one type of accompanying information of each piece of the data are associated with each other, a tree creation step of grouping a plurality of pieces of the data registered in the registration step by using the accompanying information of an optionally selected type so that pieces of the data having a common piece of the accompanying information belong to the same group, and creating a data tree virtually indicating a state in which the plurality of pieces of data are distributed into groups, and a display step of displaying a data tree created in the tree creation step on a predetermined information display device.

In a first aspect of the embodiment of the data processing method, in the registration step, a plurality of types of the accompanying information are registered in association with each of a plurality of pieces of the data, and in the tree creation step, the data tree having a hierarchical structure in which the accompanying information of a type that is higher in priority order set in advance for each type of the accompanying information is located on a higher layer is created.

In the first aspect, an order changing step of changing the priority order can be further included. In this manner, the user can optionally change a hierarchical structure of a data tree, and data management is facilitated.

A second aspect of the embodiment of the data processing method further includes a graph creation step of creating, in a case where the data is a numerical value acquired by analysis, a graph having a first axis and a second axis based on a structure of the data tree created in the tree creation step, wherein the first axis indicates each numerical value of a plurality of pieces of the data, and the second axis indicates at least one piece of the accompanying information used for the grouping based on a structure of the data tree created in the tree creation step.

An embodiment of a computer program according to the present invention is configured to execute the data processing method by being applied to an information processing device.

DESCRIPTION OF REFERENCE SIGNS

1: Data processing system
2: Information processing device
4: Information display device
6: Data acquisition device
8: Data registration part
10: Registration data holder
12: Data tree creator
14: Information display part
16: Graph creator

The invention claimed is:

1. A data processing system including an information processing device and an information display device, wherein the information processing device includes:
   at least one processor and a storage medium, the at least one processor configured to
   display a data registration screen according to a user instruction;
   request the user on the data registration screen to select a plurality of piece of data, and to input, for each selected piece of data, a plurality of types of accompanying information comprising a number of cells, an area ratio of a cell region, a number of culture days, or a passage number;
   register each of the selected pieces of data in association with the input accompanying information;
   store the registered pieces of data in the storage medium;
   group the stored pieces of data so that pieces of the data having-common accompanying information belong to the same group;
   create a data tree having a hierarchical structure in which a type of the accompanying information that is higher in a priority order is located on an upper layer;
   re-create the data tree when the user changes the priority order or disables at least one of the plurality of types of accompanying information; and
   display the data tree on the information display device, wherein the re-created data tree is displayed in real time in response to the user's change.

2. The data processing system according to claim 1, wherein the data is a numerical value acquired by analysis, and
   the at least one processor is further configured to create a graph having a first axis and a second axis based on a structure of the data tree, wherein the first axis indicates each numerical value of the plurality of pieces of data, and the second axis indicates at least one type of the accompanying information used for the grouping based on a structure of the data tree.

* * * * *